United States Patent [19]
Brown

[11] Patent Number: 5,951,563
[45] Date of Patent: Sep. 14, 1999

[54] SENSOR SYSTEM FOR FLOWABLE CEMENT

[76] Inventor: Byron L. Brown, 2315 Hendricks Blvd., Fort Smith, Ark. 72903

[21] Appl. No.: 09/169,737

[22] Filed: Oct. 8, 1998

[51] Int. Cl.$^6$ ................................... A61B 17/56
[52] U.S. Cl. ............................... 606/92; 606/94
[58] Field of Search ................... 606/92, 93, 94; 623/16, 18, 19, 26, 22, 23

[56] References Cited

U.S. PATENT DOCUMENTS

| | | | |
|---|---|---|---|
| 4,357,716 | 11/1982 | Brown | 3/1.913 |
| 5,047,061 | 9/1991 | Brown | 623/23 |
| 5,346,495 | 9/1994 | Vargas, III | 606/92 |

*Primary Examiner*—Michael Buiz
*Assistant Examiner*—Daphna Shai
*Attorney, Agent, or Firm*—Jones, Day Reavis & Pogue

[57] ABSTRACT

A sensor for enabling the viscosity of a flowable amount to be detected as it is pressurized into a sealed bone cavity section to prevent the flowable cement from passing through the intertrabecular spaces or Haversian canals in the bone cortical wall.

20 Claims, 2 Drawing Sheets

SENSOR SYSTEM FOR FLOWABLE CEMENT

BACKGROUND OF THE INVENTION

1. Field of the Invention

The present invention relates in general to the cementing of a prosthesis in a bone cavity section and specifically to a sensor for enabling the viscosity of a flowable cement to be detected as it is pressurized into the bone cavity section so as to prevent the flowable cement from passing through the intertrabecular spaces in the bone wall into the bloodstream of the patient.

2. Description of Related Art Including Information Disclosed Under 37 CFR 1.97 and 1.98

In commonly owned U.S. Pat. No. 4,357,716, incorporated hereby reference in its entirety, there is disclosed a system for mounting a femoral stem prosthesis in the femoral canal with the use of a cement.

The process includes sealing the bone cavity section in a substantially fluid-tight relationship, inserting the cement through a seal into the bone cavity under pressure, having an air escape orifice that allows air and body fluids to escape the bone cavity until it is full of cement, plugging the air escape cavity, and holding the pressure on the cement until it sets.

There are other methods of pressurizing bone cavities filled with cement. Some of them use orifices in the prosthesis itself to inject the cement under pressure.

Presently, the major compounds of bone-cement consist of a liquid monomer of methylmethacrylate, a powder, polymethacrylate, and radiopaque barium sulfate. The liquid and powder may be mixed by one of several methods and then deposited into a gun or syringe having a long nozzle. The cement is injected in a retrograde fashion, i.e. from the bottom up to near the top of the femoral canal. The initial injection of cement is somewhat timely. It should begin when the mixture is in the early doughy state. The cement should be of such viscosity that the femoral canal can be satisfactorily filled without entrapment, or at least with minimal entrapment, of air pockets. At the same time, the cement should be of such viscosity that it will partially fill the intertrabecular spaces but not flow from the intertrabecular spaces into the veins beyond the cortical bone. Usually the mixture changes from a liquid state to an early doughy state at about three minutes from beginning to mix the liquid monomer and the powder polymer.

The change from the stage when the mixture is a liquid to a slightly doughy state usually occurs in a matter of a few seconds. That period of time varies somewhat with different brands of cement. Other factors also influence the speed of this reaction or change. A variation of six degrees temperature markedly alters the speed of the reaction. A higher temperature increases the speed. Therefore, the room temperature, the overhead operating room lights, the temperature of the vial and monomer, the temperature of the package powder and the mixing bowl and the stirring ladle all influence the speed of the reaction.

Further, the method and speed of mixing affect the speed of the reaction. The greater the amount of oxygen that is mixed with the cement the more the speed of the reaction will be decreased. Most mixing is done in a container with a vacuum attached to help remove ambient vapor from the operating room. The vacuum pulls air into the mixing bowl and so the length of time that the vacuum is attached and the amount of suction influences the amount of oxygen that will pass over the mixture as well as the degree of evaporation.

Further, the monomer-polymer ratio may also have been altered which affects the speed of the reaction.

The fact is, it is extremely important for the physician to monitor the viscosity of the cement so that, when it is still in a highly liquid state, it will not be forced under pressure through the intertrabecular spaces to the veins lying beyond the cortical wall.

Presently, the physician checks the viscosity by extruding a small amount of the cement on paper and a second bit of the cement between gloved fingers. The cement is considered to be of acceptable viscosity when it no longer sticks to the glove. However, this testing is not totally reliable. Probably the two most common undetected variations are (1) the sample piece of cement does not have the same homogeneity as the cement that is injected into the canal and/or (2) the cement is cooler than normal and so the cooler cement does not have as great an adhesive property when tested as it would have at a higher temperature.

There are two methods of pressurizing cement in the femoral canal. The first method pressurizes the cement before the femoral stem is inserted and the canal is nearly filled with cement in retrograde fashion. Then, a cannulated plug, with the nozzle of the cement gun passing through the plug, is placed into the proximal end of the femoral canal and cement is applied under pressure for a limited time, usually about twenty seconds. The physician applies the amount of pressure which "feels right". It is obvious that the amount of pressure which "feels right" may vary for a physician from day-to-day as well as from one physician to another.

At the beginning of pressurization, the physician needs to know that the cement in the canal is of sufficient viscosity that it will not flow through the Haversian canals and intertrabecular spaces into the veins beyond the medullary canal and cortex.

There is also a need to know the maximum amount of pressure that can be applied to extrude the polymerizing cement without forcing the cement into the veins. The pressure which is exerted with the cannulated plug in place is estimated to be approximately 25 psi but, of course, may vary.

If the bone cavity is filled with cement under pressure first, the cannulated plug and cement gun are then removed and the prosthetic stem is then manually inserted. This temporarily increases the pressure in some areas, particularly on the concave side of the stem as the stem displaces the cement. As the stem is manually introduced, there is lateral or radial micromotion of the stem and displacement of cement. It is desired that the cement return to the immediate adjacent area of the stem from which it was displaced to form a good cement/stem connection. The return of the cement is good with cement of low-level viscosity, but diminished if the cement is moderately doughy. Then when the cement begins to expand, due to exothermic reaction, pressure is increased and some cement may rise above the femoral canal. The cement then begins to cool and shrink for about five minutes. The resultant pressure is markedly decreased after the cement has cooled and is mature. The end result is essentially that of having filled the canal and having slightly packed the cement.

The second method of pressurizing cement in the femoral canal or other bone cavity is that of inserting the prosthesis through a sealing device and inserting it in the femoral canal and attaching the sealing device to the canal or bone cavity in a substantially fluid-tight relationship and injecting cement through orifices in the sealing device. This is clearly shown in commonly owned U.S. Pat. No. 4,357,716. The sealing device in U.S. Pat. No. 4,357,716 includes an orifice for venting the canal so that air and other bodily fluids in the femoral canal can be displaced by the cement and escape through the orifice. However, when cement begins to exude from the orifice, it is then closed so that cement can no longer exude and the pressure is increased to compress the cement in an effort to remove or compress air bubbles and to cause the cement to fill the intertrabecular spaces and surround the prosthesis in a binding relationship. The hole from which the cement can exude is a one-quarter inch hole which, of course, allows the fluid products to easily flow therethrough.

Thus, when the orifice is sealed and pressure is applied, if the cement does not have sufficient viscosity, the pressure applied may force it through the intertrabecular spaces and Haversian canals and into the veins on the other side of the cortical wall.

If cement does flow into the veins on the other side of the cortical wall, there may be extremely adverse effects on the patient's health.

Thus, it would be desirable to have a more exact way of determining the viscosity of the cement to which pressure is being applied so that pressure of greater amounts than are needed or desired will not be applied when the viscosity is low and a maximal amount of pressure can be applied when the viscosity has become so great it cannot enter through the intertrabecular spaces.

SUMMARY OF THE INVENTION

The present invention is a sensor system for providing a physician an indicator of the viscosity of the cement under pressure being used for cementing a prosthesis in a bone cavity section having a cortical wall with intertrabecular spaces. Again, the bone cavity section is sealed to enclose the section in a substantially fluid-tight fashion. A first orifice is formed in the sealing means in fluid communication with the bone cavity section for injecting flowable cement into the bone cavity section. A sensor is provided in a second orifice adjacent to the first orifice and includes a hollow tube having an inside diameter larger than the intertrabecular spaces to allow pressurized cement in the bone cavity section to extrude through the hollow tube before passing through the intertrabecular spaces. The diameter is also sufficiently small so as to allow the extrusion of controlled quantities of the cement from the bone cavity section during pressurization to enable a physician to observe the cement flow viscosity as it extrudes from the hollow tube and thus regulate the amount of pressure being applied to the bone cavity section to compact the cement without forcing the cement through the intertrabecular spaces.

Because the sensor is short, having a length in the range of about 1.5 cm to about 2.5 cm and with a preferred length of 2 cm, and has an inside diameter in the range of from about 0.062 inches to 0.080 inches, that diameter is greater than the intertrabecular spaces and thus cement will be advanced more rapidly through the sensor than through the intertrabecular spaces and Haversian canals of the cortex. Pressurization of the cement is applied evenly and gradually increased. The bit of cement, which rises to the top of the sensor, should extrude as a cylindrical bead. If, however, the cement begins to flow down the outer wall of the sensor, the physician can immediately determine that the cement viscosity is too low. He can then release all pressure on the cement gun or syringe to stop the flow of cement and wait for a few seconds until the cement is more dough-like. If the first bit of cement rises as a bead in a cylindrical column beyond the tip of the sensor and then bends downwardly, pressure can be gradually increased until a bead of cement 1½ to 1⅝ inches long has been extruded through the sensor. The physician then immediately and rapidly releases pressure to stop further flow of cement. After approximately another minute, pressure is again gradually added and increased until the second bead of cement 1½ to 1⅝ inches long has been extruded. Again, pressure is rapidly decreased until the cement stops flowing. By cyclically applying pressure and releasing the pressure while observing the flow of the cement through the sensor tube, the pressure can be increased gradually with the increasing viscosity of the cement. In other words, when the cement has low viscosity, little pressure is applied and thus the cement can extrude from the sensor before it will pass through the inteftrabecular spaces. The physician can then wait 30 seconds for the cement to become more viscous then apply pressure and again observe the cement exuding from the sensor. When the cement flows down the side of the sensor, it clearly has a viscosity so low that pressure must be removed until the cement becomes more viscous. By cyclically applying the pressure and releasing the pressure while observing the cement that exudes from the sensor during pressurization, the physician can regulate the amount of pressure necessary to pressurize the cement in the bone cavity section without forcing it through the intertrabecular spaces.

Thus, it is an object of the present invention to enable a physician to pressurize cement in a bone cavity section without forcing the cement through the intertrabecular spaces and Haversian canals in the cortical wall.

It is another object of the present invention to provide a sensor with a pressurization device that allows the physician to monitor the viscosity of the cement and thus regulate the pressure needed to compress the cement without forcing it through the cortical wall of the bone section.

It is still another object of the present invention to inject cement into a bone cavity section under pressure at cyclical intervals while monitoring the viscosity of the cement to prevent the forcing of said cement through the cortical walls of the bone.

Thus, the present invention relates to a sensor system for providing a physician a visual indication of the viscosity of cement under pressure being used for cementing a prosthesis in a bone cavity section having a wall with intertrabecular spaces, the system comprising sealing means for enclosing, in a substantially fluid-tight fashion, the bone cavity section; a first orifice in the sealing means in fluid communication with the bone section for injecting flowable cement into the bone cavity section; a second orifice in the sealing means adjacent to the first orifice and in fluid communication with the bone cavity section; and a sensor means including a hollow tube mounted in the second orifice and having an inside diameter larger than the intertrabecular spaces to allow pressurized cement in the bone cavity section to extrude through the hollow tube before passing through the inteftabecular spaces, the diameter being sufficiently small to allow the extrusion of controlled quantities of the cement from the bone cavity section during pressurization to enable a physician to observe the cement flow viscosity as it extrudes from the hollow tube and regulate the amount of pressure to be applied to the bone cavity section to compact the cement without forcing the cement through the intertrabecular spaces.

BRIEF DESCRIPTION OF THE DRAWINGS

These and other features of the present invention will be more fully disclosed when taken in conjunction with the following Detailed Description of the Preferred Embodiment(s) in which like numerals represent like elements and in which.

DETAILED DESCRIPTION OF THE PREFERRED EMBODIMENT(S)

Figures 1, 2:
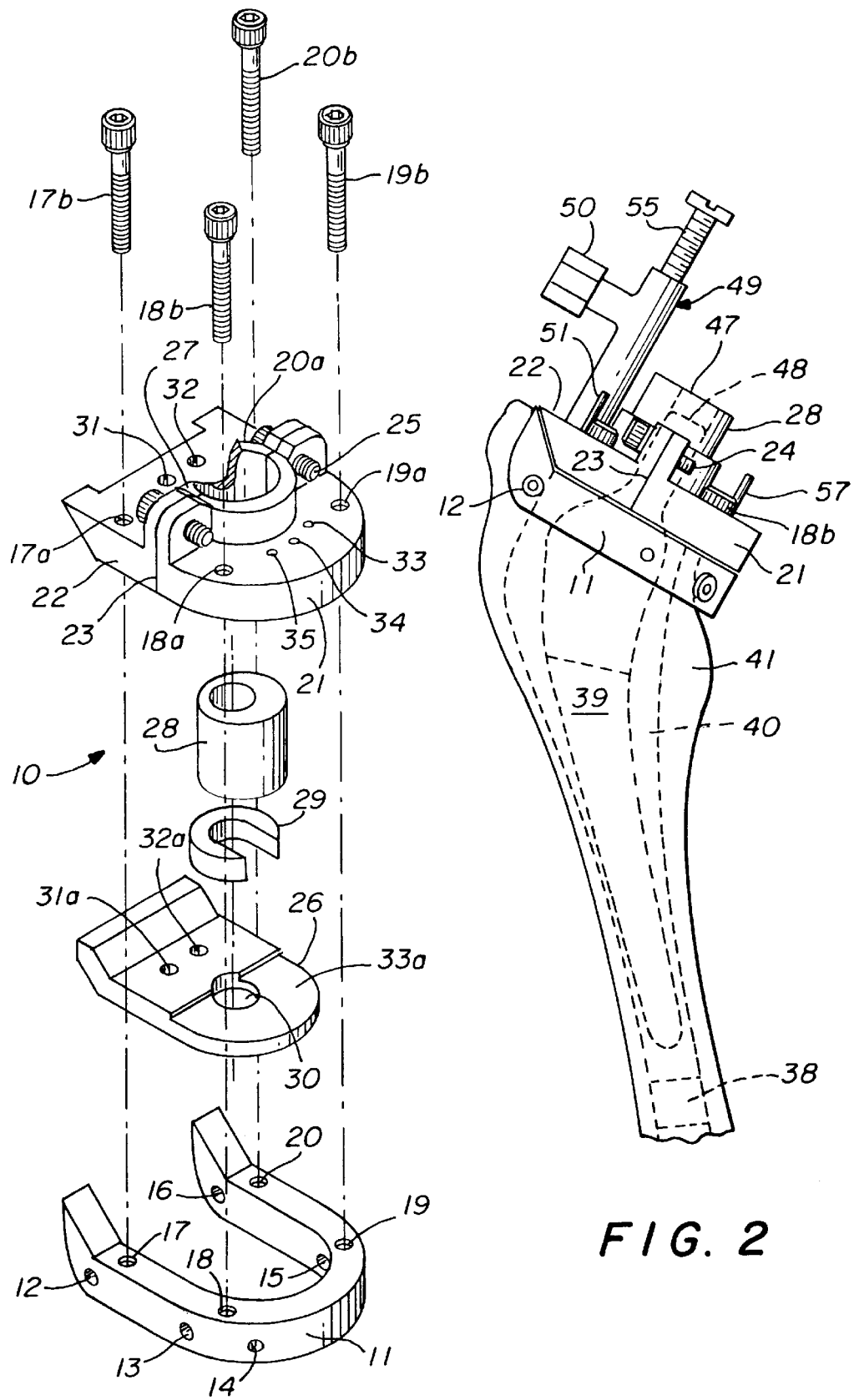
FIG. 1 is an exploded perspective view of the device for cementing a hip prosthesis in a femoral canal according to the inventive concepts hereof.
FIG. 2 is a side elevation view of the device in FIG. 1 in its assembled condition and attached to the bone cavity in condition for use in injecting cement into the bone cavity.

The device 10 of FIG. 1 is similar to the device described in commonly owned U.S. Pat. No. 5,047,061, which is incorporated herein by reference in its entirety. It is a prosthesis holding device 10 including a base guide 11, which is generally U-shaped and is described in detail in the above-referenced commonly owned patent. It includes orifices such as those shown at 12–16 in which drill bit sleeves (not shown) are inserted. Also within base guide 11 are four drilled and tapped apertures 17–20 that are positioned for registration with aligned apertures 17a–20a in ceiling halves 21 and 22. As will be observed from reference to the upper portion of FIG. 1, ceiling halves 21 and 22 are removably joined along line 23 and bolted together by threaded fastening members 24 and 25. Triple threaded bolts 17b–20b provide for completing the fastening together of the parts of FIG. 1 in tight assembly.

In addition to the above-described parts, there is a separator sealer 26 that seals the bone cavity in a substantially fluid-tight manner. Sealer 26 is preferably constructed of a plastic which is pliable to a moderate degree or may be made of a silicone elastomer. As used herein, the word "plastic" in relation to sealer 26 is inclusive of any of the foregoing materials.

A femoral stem prosthesis as shown in U.S. Pat. No. 5,047,061 has a neck that extends upwardly through opening 27 between ceiling half 21 and mating half 22. The neck is surrounded by an adjustment ring 28 and/or holding unit 29 and thence downwardly through opening 30 in separator sealer 26. Threaded apertures 31 and 32 in ceiling half 22 are provided for the temporary attachment of a syringe mechanism for the injection of prosthesis cementing material and for providing a sensor orifice during initial pressurization. It will be noted that these orifices are closely adjacent each other. This is because the physicians are cutting off the head and neck of the femur much higher resulting in a smaller circle of ellipse in which to place the inlet and outlet valves. Therefore, the orifices are reduced in size and close together. Of course, they could be moved apart as far as necessary so long as they are both in fluid communication with the bone cavity.

The device 10 can, of course, be used for inserting a prosthesis in the femoral canal of either leg of a person. In such case, if the person is lying on the left side and the prosthesis is to be inserted in the right femur, the device 10 is placed on the femur so that the orifices 31 and 32 are positioned one above the other and in like manner the orifices 33, 34, and 35 are also positioned one above the other. The cement then is injected into the bone cavity section through the lower one of the orifices 31 and 32 and the sensor 51 (shown in FIG. 2) is inserted in the upper one of the first and second orifices 31 and 32. The orifices 33, 34, and 35 are used for receiving a second sensor 57 (shown in FIG. 2). The uppermost one will be used for the second sensor 57. A needle, either 14 or 16 gauge, may be inserted through the uppermost orifice, for instance, orifice 33 and through the pliable separator sealer 26 thus forming an orifice 33a therein, and a sensor tube 57, described earlier, can then be inserted in orifice 33 through orifice 33a in the sealer 26 and into the bone cavity section.

FIG. 2 is a side view of the device of FIG. 1 in its assembled condition and attached to a femur section 41. The entire assembled device can be designated "a sealing means". The prosthesis 39 has been attached to the device as described in U.S. Pat. No. 5,047,061. A plug 38 is placed at the bottom of the bone section cavity or femoral canal 40. The base guide 11 is attached to the femur 41 and the ceiling halves 21 and 22 joined along line 23 by bolts 24 are attached to the base guide 11. The adjustment ring 28 extends upwardly through the ceiling halves 21 and 22 holding the top 48 of the prosthesis 39. Inlet valve 49 is placed in one of the orifices 31 or 32, depending upon the need as described earlier. It has a quick-disconnect 50 to which can be attached the cement gun or syringe. In the example shown in FIG. 2, the inlet valve 49 is placed in orifice 32 and a sensor 51 is placed in orifice 31 (shown in FIG. 1). A second sensor 57 is placed in orifice 33 (shown in FIG. 1).

Figure 3:
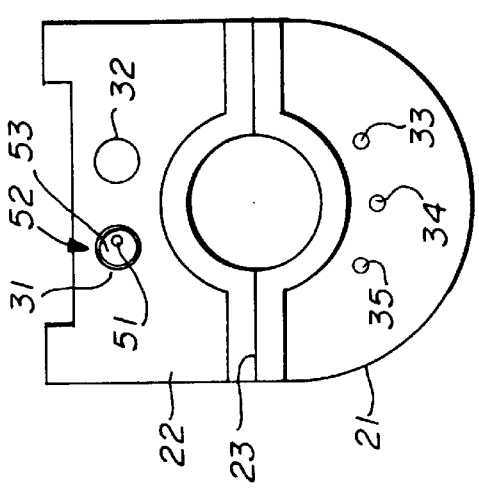
FIG. 3 is a top view of a ceiling device illustrating the sensor in one of the orifices in the ceiling.

FIG. 3 is a top view of the ceiling comprised of halves 21 and 22 joined at line 23 by bolts (shown in FIG. 1). It will be noted that a sensor device 52 in orifice 31 has an eccentrically mounted hollow sensor tube 51 held in the hollow cylinder 52 by securing means 53 such as, for example, a potting material.

Figure 4:
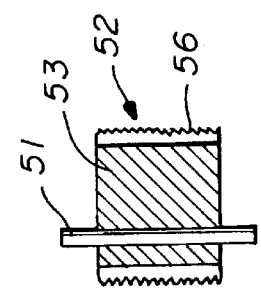
FIG. 4 is a cross-sectional view of the sensor device shown in one of the orifices of the ceiling device in FIG. 3.

A cross-sectional view of the sensor device 52 is illustrated in FIG. 4. Sensor device 52 has a hollow cylinder 56 having a threaded outer surface portion as shown for insertion in either of the first and second threaded orifices 31 and 32. It also has a hollow sensor tube 51 having a smaller outer diameter than the inside diameter of the hollow cylinder 56. A securing means 53, such as epoxy or some other wellknown material, is used to hold the hollow sensor tube 51 in rigid relationship to the hollow cylinder 56 and prevent cement from passing through the sensor device 52 except through hollow sensor tube 51. The hollow sensor tube 51 may be approximately 2 cm in length and have an inside diameter in the range of about 0.062 inches to about 0.080 inches. This inside diameter is larger than the diameter of the intertrabecular spaces or Haversian canals in the cortical wall of the femur. Thus, any cement extruding from the femoral canal, or bone cavity, will extrude through the sensor 51 before it would pass through the intertrabecular spaces. This allows the physician to observe the viscosity of the extruded cement. If the cement is "runny" or spreads downwardly and outwardly from the sensor 51, the cement has low viscosity and must be allowed to mature further, become more doughy, before pressure is again applied. Thus, "controlled quantities" of cement can be extruded from the sensor because of its inside diameter. A "large" orifice, as is now used to allow air and body fluid to escape, allows the cement to "freely" extrude with no substantial pressure buildup in the bone cavity. The inside diameter of the present, novel sensor tube, although larger than the intertrabecular spaces, is small enough to allow cement to be extruded therefrom under pressure buildup in the bone cavity section.

It will be noted that the securing means 53 attaches the hollow sensor tube 51 to the inside of the hollow cylinder 56 in an eccentric relationship. This allows the hollow cylinder 56 to be rotated in orifice 31 or 32 to move the hollow sensor tube 51 to its furthest position to the adjacent orifice 31 or 32. Thus the hollow sensor tube 51 can be positioned in any desired circular relationship within orifice 31 or 32 so that it can be adjusted to fit a bone cavity section of varying diameter to keep the sensor 51 as far from the injection orifice as possible to prevent it from becoming plugged with cement.

Figure 5:
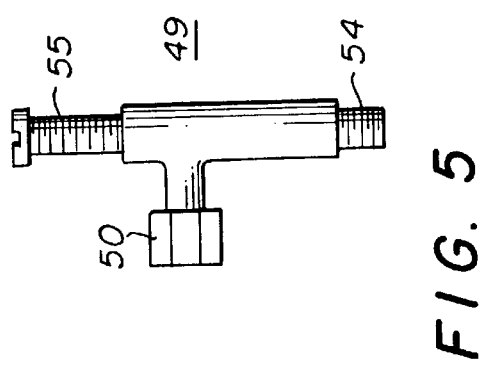
FIG. 5 is a side view of the cement injection valve for inserting in the other orifice of the ceiling device shown in FIG. 3 for injecting cement therein.

FIG. 5 is a side view of the injection valve 49, which has a threaded end 54 that can be threadedly engaged with either of the orifices 31 or 32. It also has a quick-disconnect valve 50 that allow the cement gun or syringe to be quickly attached to and detached from the injection valve 49. It also has a threaded plunger 55 that can be used to force all of the cement out of the injection valve 49 into the bone cavity such as the femoral canal.

The invention operates as follows. The bone cavity section is partially filled with flowable cement to such a level that insertion of the prosthesis in the bone cavity section will not cause the cement level to rise to the top of the bone cavity section. The prosthesis is then attached to the device 10 shown in FIG. 1 and illustrated in FIG. 2 and the prosthesis is inserted in the bone cavity with the sealing device enclosing the bone cavity section in a fluid-tight manner. Cement is injected into the bone cavity section under pressure at cyclical intervals until the cement as set. First, the cement is injected into the bone cavity section under pressure until a bead of cement is extruded from either the first sensor tube 51 or the second sensor 57 inserted in orifice 33. Should the first sensor tube 51 become covered with cement, the more remotely positioned second sensor 57 in one of orifices 33, 34, or 35 will exude air and body fluids until the cement has totally filled the bone cavity section. Then it will exude from one of the two sensors 51, 57 where it can be checked by the physician for its viscosity. Since there are two spaced input orifices 31 and 32 and three spaced orifices 33, 34, and 35 that can be used for a second sensor tube 57, the device allows a physician to use it when replacing a hip on either the right or the left side as described earlier. The appropriate ports can then be selected.

Figure 6:
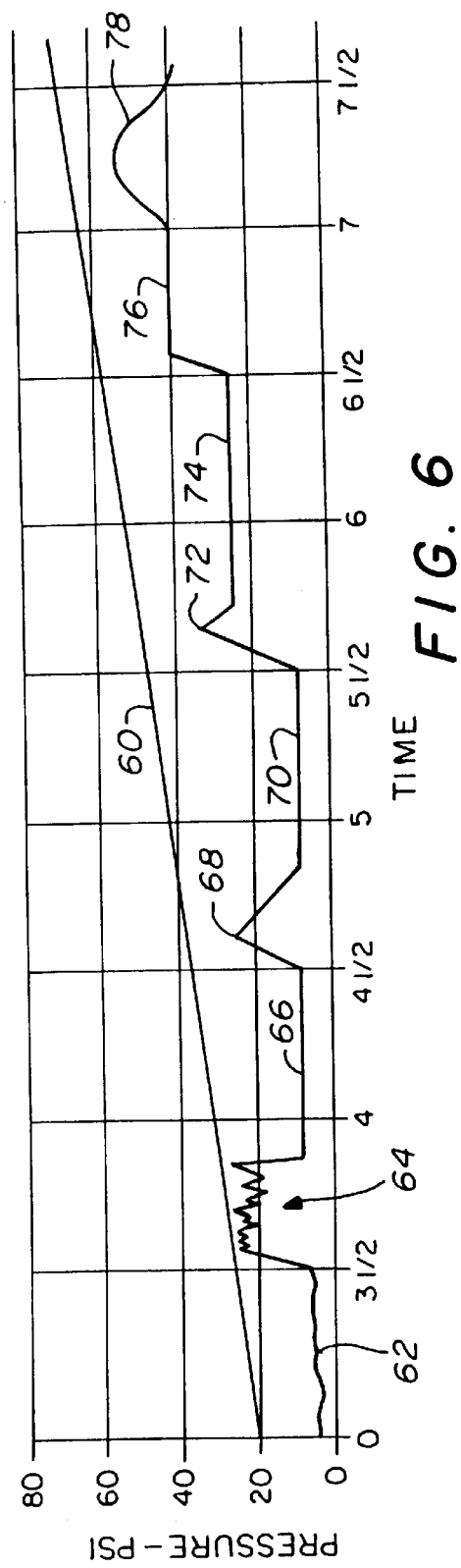
FIG. 6 is a time pressure graph representing a typical pressurization cycle of the cement.

FIG. 6 is a graph of pressure versus time illustrating the principle of the present invention. It is not intended to be exact, but is an example only to illustrate the principle. As can be seen in FIG. 6, the linear line 60 indicates that with increasing time it takes ever-increasing pressure to force the cement through the intertrabecular spaces because the cement is becoming more and more viscous. Clearly, then, when the cement is the least viscous, as shown during the first 3½ minutes, the pressure that is applied should be a minimum to keep from forcing the cement through the intertrabecular spaces.

The time scale actually begins with the time from beginning to mix the cement. Thus, after the cement has been mixed and inserted into the bone cavity section, there is an area 62 with a small amount of pressure generated inside the bone cavity. At 3½ minutes after mixing and with the bone cavity section being filled with cement to a point below the top of the bone section, the prosthesis is inserted at 64 and the insertion increases the pressure within the canal. Then by waiting until 4½ minutes after mixing of the cement, the pressure at 66 is increased to a point at 68 until a cement bead 1½ to 1¾ inches long has been extruded from the flow sensor. All pressure is then released by removing the pressure on the cement being injected. Tests have shown that the pressure on the cement will have reached approximately 25 psi and releasing the pressure will drop the pressure in the canal to under 10 psi as shown at 70. Of course, if the cement stops flowing from the sensor at any time during this process when cement is being added, one must assess whether the plug at the distal end is leaking, the seal between the apparatus and the cortex is leaking, or there is a hole or break in the femoral canal. If none of the three possibilities exists, then the cement is maturing much faster than usual and cement must be added until a bead 3½ to 4 inches long has been extruded and then immediately close the inlet valve.

Otherwise, at approximately 5½ minutes from beginning to mix the cement, pressurized cement is added again until a second bead 1 to 1½ inches long has been extruded. Then pressure is gradually released until the cement stops flowing from the sensor. This time, the pressure will have reached approximately the 34 or 35 psi as shown as 72. The pressure will then fall and remain as shown as 74. At about 6½ minutes after mixing the cement, add pressure so as to extrude a ½ to ⅝ inch bead of cement. Usually the cement from the sensor at this time will stop flowing when one stops adding cement. Therefore, a release of the gun pressure is not done. The pressure will be approximately 40 psi as shown at 76. The threaded piston in inlet valve is then moved inwardly to clear the cement from the injection valve, which adds approximately 1½ to 1¾ cc of cement to the femoral canal causing the pressure to rise to approximately 50 psi as shown at 78.

Pressuring cement to even greater pressures may improve the quality of the mature cement; however, there is evidence that indicates that pressurization which is greater than 60 psi probably has little or no effect in improving the quality of the cement or of improving fixation.

The present invention could be used to initially fill the femoral canal with cement. A sealer could be used to seal the bone cavity. One orifice can be used to inject cement into the sealed cavity while the sensor, in a second orifice, provides the physician the necessary indication of cement viscosity as previously explained.

It will be noted that the procedure still requires the judgment and skill of the physician but, with the sensor of the present invention, the physician knows the viscosity of the cement in the bone cavity and can then make reasonable adjustments in pressure to get the maximum compression of the cement in the bone cavity while maintaining a pressure that will not force the cement through the cortical walls of the bone cavity.

Thus, there has been disclosed a sensor system for providing a physician an indication of the viscosity of cement under pressure being used for cementing a prosthesis in a bone cavity section having a wall with intertrabecular spaces and/or Haversian canals. The bone cavity section is enclosed with a sealing means in a substantially fluid-tight fashion. Flowable cement is injected in a first orifice in the sealing means and in fluid communication with the bone cavity section. At least one sensor is provided in the sealing means in a second orifice adjacent the first orifice and in fluid communication with the bone cavity section. The sensor has a hollow tube mounted therein and has an inside diameter larger than the intertrabecular spaces so as to allow pressurized cement in the bone cavity section to always extrude through the hollow tube before passing through the intertrabecular spaces. The inside diameter of the tube is sufficiently small to allow the extrusion of controlled quantities of cement from the bone cavity section during pressurization to enable a physician to observe the cement flow viscosity as it extrudes from the hollow tube and thus enable the physician to regulate the amount of pressure to be applied to the bone cavity section to compact the cement in the bone cavity section without forcing the cement through the intertrabecular spaces.

The corresponding structures, materials, acts, and equivalents of all means or step plus function elements in the claims below are intended to include any structure, material, or act for performing the function in combination with other claimed elements as specifically claimed.

I claim:

1. A sensor system for providing a user an indication of the viscosity of flowable cement under pressure being used for cementing a prosthesis in a bone cavity section having a wall with intertrabecular spaces, said system comprising:

sealing means for enclosing, in a substantially fluid-tight fashion, said bone cavity section;

a first orifice in said sealing means in fluid connection with said bone cavity section for injecting flowable cement into said bone cavity section;

a second orifice in said sealing means adjacent said first orifice and in fluid communication with said bone cavity section; and sensor means including a hollow tube mounted in said second orifice, said hollow tube having an inside diameter larger than said intertrabecular spaces to allow pressurized cement in said bone cavity section to extrude through said hollow tube before passing through said intertrabecular spaces, said diameter being sufficiently small to allow the extrusion of controlled quantities of said cement from said bone cavity section during pressurization to enable a physician to observe the cement flow viscosity as it extrudes from said hollow tube and regulate the amount of pressure to be applied to said bone cavity section according to said cement viscosity to compact said cement without forcing said cement through said intertrabecular spaces.

2. The sensor system of claim 1 wherein said first and second orifices are interchangeable in use such that the cement can be injected into said bone cavity section through said second orifice and said hollow tube sensor can be placed in said first orifice.

3. The sensor system of claim 2 wherein said first and second orifices are threaded.

4. The sensor system of claim 3 wherein said hollow tube sensor comprises:

a hollow cylinder having a threaded outer surface portion for insertion in either of said first and second threaded orifices;

a hollow tube having a smaller outer diameter than the inside diameter of said hollow cylinder; and securing means for attaching said hollow tube to the inside of said hollow cylinder in a fluid-tight relationship.

5. The sensor system of claim 4 wherein said securing means attaches said hollow tube to the inside of said hollow cylinder in an eccentric relationship such that by rotating said hollow cylinder in one of said first and second orifices, said hollow tube can be moved closer to or further away from the other one of said first and second orifices through which said cement is to be injected.

6. The sensor system of claim 5 further comprising an inlet valve for threadable insertion in either of said first and second orifices for receiving flowable cement from a pressurizing device and conveying said cement to said bone cavity section under pressure.

7. The sensor system of claim 6 wherein said hollow tube of said sensor comprises:

a length in the range of from about 1.5 cm to about 2.5 cm; and an inside diameter in the range of from about 0.062 inch to about 0.080 inch.

8. The sensor system of claim 1 further comprising:

at least one additional orifice in said sealing means spaced remotely from said first and second orifices;

a rubberized gasket forming part of and being located under said sealing means; and a second sensor having dimensions comparable to said hollow tube for removable insertion through said additional orifice and said rubberized gasket to enable air and body fluids to escape said bone cavity section as said cement is injected therein under pressure thus allowing said controlled quantities of cement to be extruded only after said bone cavity section is filled with cement.

9. A method of providing a user an indicator of pressure being applied to a flowable cement used for cementing a prosthesis in a bone cavity section that has a top and a bottom and having a wall with intertrabecular spaces, said method comprising the steps of:

enclosing said bone cavity section in a substantially fluid-tight manner with a sealing device;

injecting flowable cement into said bone cavity section through a first orifice in said sealing device in fluid communication with said bone cavity section;

including a second orifice in said sealing device adjacent said first orifice and in fluid communication with said bone cavity section;

mounting a first sensor means, including a hollow tube, in said second orifice;

providing said hollow tube with an inside diameter larger than said intertrabecular spaces to allow pressurized flowable cement injected in said bone cavity section to extrude through said hollow tube before passing through said intertrabecular spaces; and said hollow tube inside diameter being sufficiently small to allow extrusion of controlled quantities of said pressurized cement from said bone cavity section during pressurization thereof to enable a physician to observe the cement flow viscosity as it extrudes from said hollow tube to determine the amount of pressure to be applied to said cement in said bone cavity section to compact said cement without forcing said cement through said intertrabecular spaces.

10. The method of claim 9 further including the step of forming said first and second orifices for interchangeable use such that the cement can be injected into said bone cavity section through said second orifice and said hollow tube sensor can be placed in said first orifice.

11. The method of claim 10 further comprising the step of threading said first and second orifices.

12. The method of claim 11 further comprising the steps of:

threading at least a portion of the outer surface of a hollow cylinder for insertion in either of said first and second orifices; and securing a hollow tube, having a smaller outside diameter than the inside diameter of said hollow cylinder, to the inside of said hollow cylinder in a fluid-tight relationship.

13. The method of claim 12 further comprising the step of securing said hollow tube to the inside of said hollow cylinder in an eccentric relationship such that by rotating said hollow cylinder in one of said first and second orifices, said hollow tube can be moved to a desired position with respect to the other one of said first and second orifices through which said cement is to be injected.

14. The method of claim 13 further comprising the step of injecting flowable cement into said bone cavity section under pressure through an inlet valve threadedly inserted in either of said first and second orifices.

15. The method of claim 14 further comprising the step of forming said hollow sensor tube of a length in the range of from about 1.5 cm to about 2.5 cm and having an inside diameter in the range of from about 0.062 inch to about 0.080 inch.

16. The method of claim 9 further comprising the steps of:
providing at least one additional orifice in said sealing device spaced remotely from said first and second orifices;
placing a rubberized gasket as part of and under said sealing device; and
removably inserting a second hollow sensor tube through said additional orifice and said rubberized gasket to ensure that air and body fluids escape said bone cavity section as said cement is injected therein under pressure thus allowing said controlled quantities of cement to be extruded only after said bone cavity section is filled with cement.

17. The method of claim 16 further comprising the steps of:
providing three of said additional orifices in said sealing device substantially diametrically opposite said first and second orifices and in spaced relationship to each other;
placing said sealing device on said bone cavity section such that said first and second orifices are positioned one above the other and said three spaced additional orifices are positioned one above the other;
injecting said cement into said bone cavity section through the lower one of the first and second orifices;
inserting said hollow sensor tube into the upper one of said first and second orifices; and
inserting said second hollow tube sensor in the upper most one of said three additional orifices to allow said air and body fluids to escape said bone cavity section as said cement is injected therein under pressure.

18. The method of claim 16 further comprising the step of filling said bone cavity section with flowable cement to a level such that insertion of the prosthesis in the bone cavity section will not cause the cement level to rise to the top of said bone cavity section.

19. The method of claim 18 further comprising the steps of:
inserting said prosthesis in said bone cavity section with said sealing device enclosing said bone cavity section in said substantially fluid-tight manner; and
injecting cement into said bone cavity section under pressure at cyclical intervals until said cement has set.

20. The method of claim 19 wherein the step of cyclically injecting cement into said bone cavity section further comprises the steps of:
(a) injecting cement into said bone cavity section under pressure until a bead of cement is extruded from one of said hollow tube sensors;
(b) reducing the pressure sufficient to stop the extrusion of said cement from said sensor;
(c) resuming said cement injection under pressure if said extruded bead of cement has a portion in the form of a cylindrical column;
(d) ceasing pressurization for a first period of time if said extruded cement spreads out from said sensor laterally;
(e) resuming injection of said cement under pressure after said first period of time until a second bead of cement extrudes from one of said sensors; and
(f) repeating steps (d) and (e) until said extruding cement appears as a cylindrical column and stops flowing when pressurization ceases.

* * * * *